United States Patent
Marron et al.

(10) Patent No.: US 10,049,419 B1
(45) Date of Patent: Aug. 14, 2018

(54) MOBILE LAW ENFORCEMENT COMMUNICATION SYSTEM AND METHOD

(71) Applicant: MOTOROLA SOLUTIONS, INC, Chicago, IL (US)

(72) Inventors: Alex Marron, Davie, FL (US); Anthony J. Suppelsa, Parkland, FL (US); Barbara R. Doutre, Plantation, FL (US)

(73) Assignee: MOTOROLA SOLUTIONS, INC., Chicago, IL (US)

( * ) Notice: Subject to any disclaimer, the term of this patent is extended or adjusted under 35 U.S.C. 154(b) by 0 days.

(21) Appl. No.: 15/696,827

(22) Filed: Sep. 6, 2017

(51) Int. Cl.
| | |
|---|---|
| *H04N 7/14* | (2006.01) |
| *G06Q 50/26* | (2012.01) |
| *H04L 29/06* | (2006.01) |
| *A61B 5/08* | (2006.01) |
| *A61B 5/1172* | (2016.01) |
| *G06F 9/451* | (2018.01) |
| *A61B 5/1171* | (2016.01) |
| *G06K 9/00* | (2006.01) |
| *G06Q 50/18* | (2012.01) |
| *G06Q 20/14* | (2012.01) |

(Continued)

(52) U.S. Cl.
CPC ............ *G06Q 50/26* (2013.01); *A61B 5/082* (2013.01); *A61B 5/1172* (2013.01); *G06F 9/453* (2018.02); *H04L 65/1069* (2013.01); *H04L 65/403* (2013.01); *H04N 7/142* (2013.01); *H04N 7/147* (2013.01); *A61B 5/1176* (2013.01); *A61B 5/167* (2013.01); *G06F 17/30424* (2013.01); *G06K 9/00013* (2013.01); *G06K 9/00288* (2013.01); *G06K 9/00335* (2013.01); *G06Q 20/14* (2013.01); *G06Q 50/18* (2013.01)

(58) Field of Classification Search
CPC ..... A61B 5/082; A61B 5/1172; A61B 5/1176; A61B 5/167; G06F 9/4446; G06F 17/30424; G06K 9/00013; G06K 9/00288; G06K 9/00335; G06Q 20/14; G06Q 50/18; G06Q 50/26; H04L 65/1069; H04L 65/403; H04N 7/142; H04N 7/147
USPC ................................ 348/14.01, 14.02, 14.03
See application file for complete search history.

(56) References Cited

U.S. PATENT DOCUMENTS

| 3,977,680 A | * | 8/1976 | Lavine ................ A63F 3/00138 |
| | | | 273/249 |
| 4,965,819 A | | 10/1990 | Kannes |

(Continued)

OTHER PUBLICATIONS

Matthew Terry, Dr. Steve Johnson and Peter Thompson: "Virtual Court pilot Outcome evaluation", Ministry of Justice Research Series 21/10, Dec. 2010, all pages.

(Continued)

*Primary Examiner* — Khai N Nguyen
(74) *Attorney, Agent, or Firm* — Barbara R. Doutre (57) ABSTRACT

A communication system (200) provides a self-driving vehicle (122) having a plurality of processor controlled interface devices (230) that acquire input pertaining to a detainee and an infraction associated with the detainee located within the vehicle. The processor controlled interface devices (230) provide mobile law enforcement processing and proceedings of the detainee within the self-driving vehicle (122). The self-driving vehicle (122) automatically delivers the detainee to an approved location determined by the mobile law enforcement processes and proceedings.

22 Claims, 3 Drawing Sheets

(51) Int. Cl.
  *G06F 17/30* (2006.01)
  *A61B 5/16* (2006.01)

(56) References Cited

U.S. PATENT DOCUMENTS

| | | | | |
|---|---|---|---|---|
| 5,797,134 | A * | 8/1998 | McMillan | G06Q 30/0283 705/4 |
| 7,061,521 | B2 | 6/2006 | Bulriss et al. | |
| 7,307,651 | B2 | 12/2007 | Chew | |
| 7,511,833 | B2 * | 3/2009 | Breed | G01F 23/0076 180/272 |
| 7,529,357 | B1 * | 5/2009 | Rae | H04M 3/38 370/261 |
| 8,320,893 | B2 | 11/2012 | Suurmeyer et al. | |
| 8,477,662 | B2 | 7/2013 | Schneider | |
| 8,667,162 | B2 * | 3/2014 | Yu | H04L 65/605 348/14.01 |
| 9,124,763 | B2 | 9/2015 | Humphries | |
| 9,429,947 | B1 * | 8/2016 | Wengreen | G05D 1/0016 |
| 9,811,989 | B2 * | 11/2017 | Austin | G08B 13/19602 |
| 9,819,756 | B1 * | 11/2017 | Welker-Muraguri | H04L 67/26 |
| 2006/0129445 | A1 * | 6/2006 | McCallum, Jr. | G06Q 10/10 705/7.18 |
| 2006/0197672 | A1 * | 9/2006 | Talamas, Jr. | A01K 15/023 340/573.3 |
| 2007/0156317 | A1 * | 7/2007 | Breed | B60N 2/002 701/45 |
| 2009/0281943 | A1 | 11/2009 | Yoggerst | |
| 2011/0196723 | A1 | 8/2011 | Baszucki et al. | |
| 2011/0320370 | A1 * | 12/2011 | Henry, Jr. | B60R 25/305 705/311 |
| 2013/0046700 | A1 | 2/2013 | Vilosny | |
| 2014/0254896 | A1 * | 9/2014 | Zhou | B25J 9/0006 382/124 |
| 2015/0051502 | A1 * | 2/2015 | Ross | H04N 5/772 600/532 |
| 2015/0149370 | A1 | 5/2015 | Klein et al. | |
| 2016/0027134 | A1 | 1/2016 | Alvarado et al. | |
| 2016/0125735 | A1 * | 5/2016 | Tuukkanen | G08G 1/09 701/23 |
| 2016/0251081 | A1 * | 9/2016 | Staskevich | B64C 39/024 701/2 |
| 2016/0307156 | A1 * | 10/2016 | Burner | G06Q 10/10 |
| 2016/0358017 | A1 * | 12/2016 | Guzik | G06K 9/00832 |
| 2016/0363582 | A1 * | 12/2016 | Blackley | G01N 33/497 |
| 2017/0024986 | A1 * | 1/2017 | Austin | G08B 21/12 |
| 2017/0075358 | A1 * | 3/2017 | Zhang | G06Q 10/06 |
| 2017/0083878 | A1 * | 3/2017 | Conrad | G06Q 20/0855 |
| 2017/0132737 | A1 * | 5/2017 | Boss | G06Q 50/26 |
| 2017/0295279 | A1 * | 10/2017 | Rokosky | H04M 3/2281 |
| 2017/0300053 | A1 * | 10/2017 | Wengreen | G05D 1/0088 |
| 2017/0345084 | A1 * | 11/2017 | Gordon | G06Q 30/0639 |
| 2018/0018869 | A1 * | 1/2018 | Ahmad | G05D 1/0088 |

OTHER PUBLICATIONS

Telegraph View, "Vitual courts could deliver real justice", Feb. 16, 2015, http://www.telegraph.co.uk/news/uknews/law-and-order/11414466/Virtual-courts-could-deliver-real-justice.html, downloaded from internet: Jul. 31, 2017.

"Cisco Mobile Network Solutions", Cisco 3200 Series Rugged Integrated Service Routers, White Papers, Updated: Apr. 8, 2008, Document ID: 1477020318104181, http://www.cisco.com/c/en/us/products/collateral/routers/3200-series-rugged-integrated-services-routers-isr/prod_white_paper0900aecd806220af.html, downloaded from the internet: Jul. 31, 2017, all pages.

"Put Microsoft Office into your car", Office Watch, Jan. 7, 2016, https://office-watch.com/2016/put-microsoft-office-into-your-car/, downloaded from the internet: Jul. 31, 2017, all pages.

Davies, Chris: "Renault NEXT TWO self-driving car could be on roads by 2020", https://www.slashgear.com/renault-next-two-self-driving-car-could-be-on-roads-by-2020-06316044/, downloaded from internet: Jul. 31, 2017, all pages.

"Connected Justice: Bring the Courtroom to the Prisoner", Newsletter Article, Cisco, http://www.cisco.com/c/dam/en_us/solutions/industries/docs/gov/govtconnection121510connjustice.pdf, copyright 1992-2010 Cisco Systems, Inc., downloaded from internet: Jul. 31, 2017, all pages.

"Cisco Connected Justice: Connecting Law Enforcement, Courts, and Corrections", Connected Justice, Updated Aug. 2012, http://www.cisco.com/c/dam/en_us/solutions/industries/docs/gov/conc_justicelaw_enforce.pdf, downloaded from internet: Jul. 31, 2017, all pages.

"Video for Public Safety and Justice: Five Stragegies to Stretch Government Budgets", CISCO White Paper, http://www.cisco.com/c/dam/en/us/products/collateral/physical-security/video-surveillance-storage-system/strategies_stretch_govt_budgets.pdf, 2012 Cisco, downloaded form internet: Jul. 31, 2017.

Racicot, Desmond J: "How Police Departments are Harnessing Technology to Make a Difference", Cisco Blogs>Government, https://blogs.cisco.com/government/how-police-departments-are-harnessing-technology-to-make-a-difference, Feb. 21, 2017, downloaded from internet: Jul. 31, 2017, all pages.

"Video for Public Safety and Justice: Five Strategies to Stretch Government Budgets", Cisco White Paper, 2012 Cisco, http://www.cisco.com/c/dam/en/us/products/collateral/physical-security/video-surveillance-storage-system/strategies_stretch_govt_budgets.pdf, downloaded from internet: Jul. 31, 2017, all pages.

"Opportunities Are All Around You for a Safer Community", Cisco 2015, https://www.slideshare.net/CiscoBusinessInsights/public-safety-and-ioe-safer-communities, all pages.

Singh, Dr.S.N, et al.: FPGA Based Autonomous Vehicle Locking System—A Smart Door Lock, Review Paper, International Journal of Recent Trends in Engineering, vol. 2, No. 4, Nov. 2009, https://www.researchgate.net/publication/238742915_FPGA_Based_Autonomous_Vehicle_Locking_System_A_Smart_Door_Lock, all pages.

Chris Johnston and Agencies: "Artificial intelligence 'judge' developed by UCL computer scientists", Technology, The Guardian, https://www.theguardian.com/technology/2016/oct/24/artificial-intelligence-judge-university-college-london-computer-scientists, Sunday Oct. 23, 2016, downloaded from the internet: Aug. 1, 2017, all pages.

* cited by examiner

MOBILE LAW ENFORCEMENT COMMUNICATION SYSTEM AND METHOD

FIELD OF THE DISCLOSURE

The present disclosure relates generally to communication systems and more particularly to facilitating processes and proceedings associated law enforcement communication systems.

BACKGROUND

The desire to maintain effective communications is paramount when operating in public safety environments and particularly in law enforcement communication environments. The processes and proceedings involved in law enforcement communications are oftentimes complex and time consuming. The system can often be plagued by minor incidents or infractions taking up law enforcement resources, holding facility space, and court time.

Accordingly, there is a need for an improved approach to processing minor incidents or infractions in an efficient and expedient manner.

BRIEF DESCRIPTION OF THE FIGURES

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

The system and method components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein.

DETAILED DESCRIPTION

Briefly, there is provided herein a communication system performing mobile law enforcement processes and proceedings of a detainee. The communication system comprises a self-driving vehicle, a plurality of interface devices, and an electronic processor located within the self-driving vehicle. The processor controlled interface devices are configured to acquire input information pertaining to a detainee located within the self-driving vehicle and an infraction associated with the detainee. The electronic processor is programmed to receive the acquired input pertaining to the detainee and infraction, and in response thereto, enable mobile law enforcement processes and proceedings via the plurality of interface devices. The self-driving vehicle delivers the detainee to an approved location determined by the mobile law enforcement processes and proceedings.

During a typical detention scene, an officer temporarily stops an individual for questioning, without transporting the individual to another location. A detention stop allows the officer to determine whether to make an arrest, investigate further, or take no further action. In accordance with some embodiments, the processing provided by the mobile law enforcement communication system to be described herein can be used as an initial test hub for suspected infractions of alcohol, weapons and/or drug use.

Figure 1:
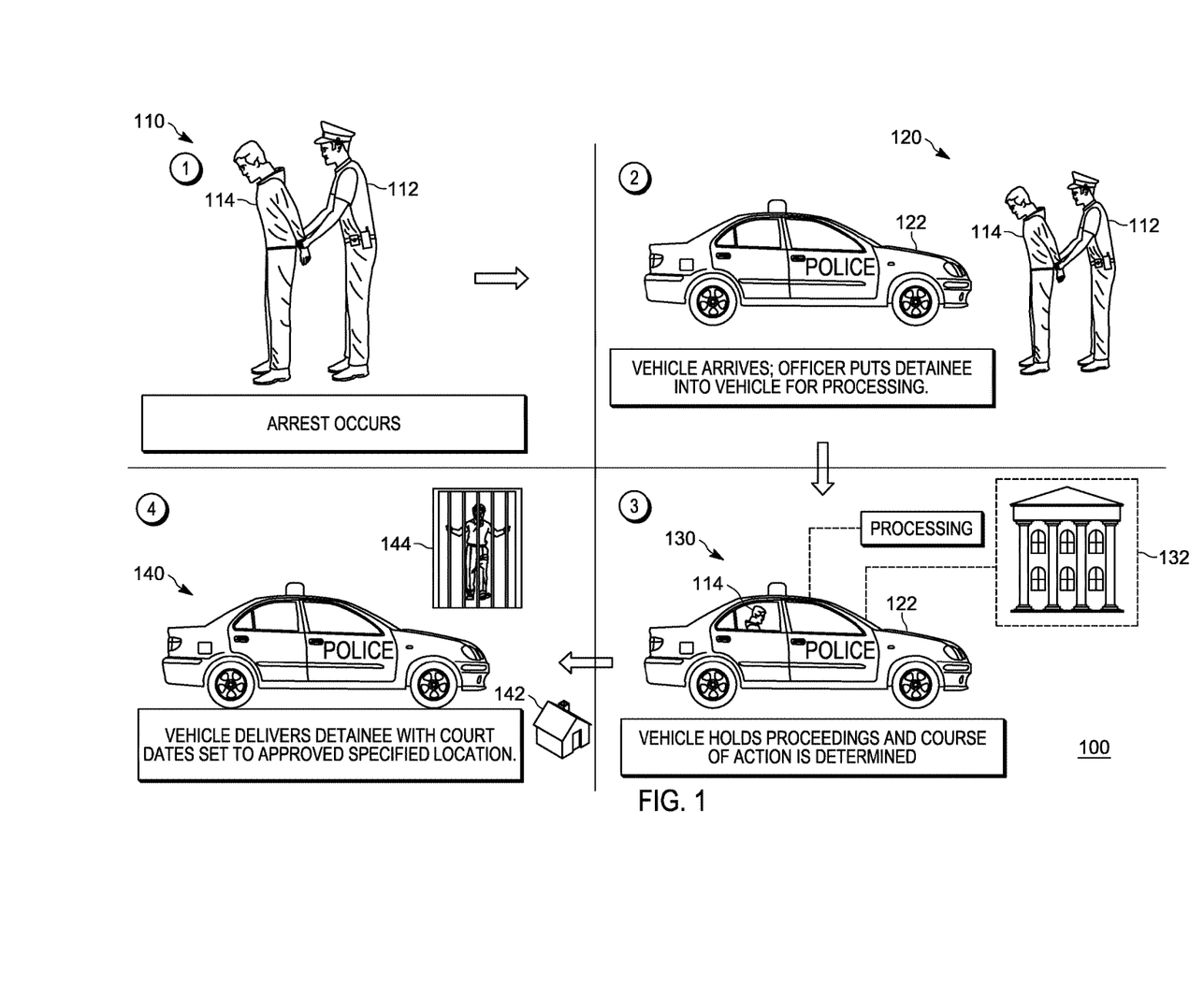
FIG. 1 shows law enforcement processes and proceedings of a mobile communication system formed and operating in accordance with some embodiments.

A detention may lead to an arrest, where the individual is taken into custody and is no longer free to leave. In the past, an individual might have been taken into custody by having the officer drive him back to a police station. However, in accordance with the embodiments, FIG. 1 shows law enforcement processes and proceedings of a mobile communication system 100 formed and operating in accordance with some embodiments. By performing law enforcement processes and proceedings within a vehicular environment, an officer 112 is able to remain in the field, thereby advantageously preserving law enforcement resources.

In response to an arrest taking place at 110, a self-driving vehicle 122 (also referred to as an autonomous vehicle) arrives on scene at 120, where the detained or arrested individual (both shall be referred to as a detainee) is placed into the self-driving vehicle 122 for initial processing. Depending on the type of incident or alleged infraction, the individual may or may not remain handcuffed within the vehicle, but is detained within at least a portion of the vehicle throughout the process, such as a backseat area. In accordance with the embodiments, predetermined law enforcement processes and proceedings take place at 130 using the autonomous vehicle's communication system.

Depending on the severity of the incident or alleged infraction, the processes and proceedings taking place within the self-driving vehicle 122 may take the form of one or more of testing, booking, arraignment, and even full adjudication, if applicable. For example, the mobile communication system 100 can be used as a mobile test hub for determining alcohol levels, drugs, and/or weapons. Sensors and scanners plugged in within the self-driving vehicle 122 provide preliminary in-vehicle screening tools to help law enforcement officers assess a driver suspected of being drunk, carrying a dangerous or weapon, and predetermined drugs. As air sensors and scanners continue to evolve, the detained individual may simply remain within the vehicle while the tests are processed, analyzed, and results communicated to one or more appropriate recipients. Depending on the status of the detainee's confinement, results may be communicated, over one or more wireless communications networks, to law enforcement, a remote attorney, and/or an on-call judge which may be contacted by the communication as part of the mobile processes and proceedings.

The law enforcement processing and proceedings of the detainee taking place at 130 may comprise a plurality of activities, which may vary from incident to incident and jurisdiction to jurisdiction. The processes and proceedings comprise for example, testing for alcohol levels, drugs, and/or weapons, an automated reading and display of legal rights in the detainee's primary language, automated camera photo, image recognition, fingerprint scanning, outstanding warrant searches, booking proceedings, arraignment proceedings, adjudication proceedings, bail processing, and/or fine payment processing.

Depending on the infraction, the order of the processing may be varied. For example, the testing for drugs and/or alcohol may be part of an initial detention, followed by an arrest as a result of affirmative test results. In accordance with some embodiments, the arrest of an individual and placement within the vehicle is followed by communication system providing the detainee with a reading and visual presentation of legal rights in the detainee's primary language.

In accordance with the embodiments, the mobile communication system 100 at 130 provides, as part of the law enforcement proceedings, a reading and visual presentation of a person's legal rights in the detainee's primary language. The arrested individual 114 may invoke a right to counsel verbally to the communication system. In response to the verbal instruction, the mobile communication system assigns an attorney or contacts the detainee's individual attorney (based on verbal input from the detainee, such as attorney name and/or law firm). The autonomous vehicle's communication system can then join communications between the remote attorney and the detainee 114. These communications taking place between only the remote attorney and the detainee 114 would not be recorded and would be considered attorney client privileged.

Depending on the alleged infraction or incident, the processes and proceedings performed at 130 by the self-driving vehicle 122 on the arrested individual 114 may further trigger and expedite other law enforcement processes. For example, if weapons (metal) or drugs or alcohol are detected, there may be sufficient cause for a warrant of the individual's car, home, or place of business. In response to the vehicular communication system detecting weapons or illegal drugs or exceeded alcohol level thresholds, a warrant request may automatically be submitted to and reviewed real time by a remote, on-call judge contacted by the vehicular communication system. The ability to have search warrants approved while the detainee is located in the vehicle saves considerable time and minimizes disruption in preserving evidence.

The communication system 100 minimizes paperwork in that the real time questions, answers, test results, and law enforcement processes and proceedings can (where not excluded by attorney client privilege) be automatically recorded, transcribed, and saved to a memory of the communication system.

Further processing taking place at 130 may comprise an arraignment proceeding using the autonomous vehicle's communication system. The arraignment is typically a criminal proceeding at which the defendant is informed of the offense charged, and asked to enter a plea. In accordance with the various embodiments, the arraignment can take place using the autonomous vehicle's communication system which joins communications between an on-call judge, a remote attorney, and the arrested individual 114. The detainee may enter a plea of for example, guilty, not guilty, or as other applicable option (for example: no contest), as appropriate to the incident. The arraignment process further determines whether the detainee is to be released on his own recognizance, taken to an approved location, such as a home or shelter, taken to a police station for further questioning, or taken directly to jail. These mobile proceedings taking place between the on-call judge, the remote attorney, and the detainee within the self-driving vehicle are stored in a memory of the communication system 100 as part of a court proceeding record.

As part of the processing and proceedings taking place at 130, the vehicular communication system may be used to further facilitate the arraignment proceedings in which bail is set by the on-call, remote judge participating in the proceedings. Options pertaining to posting the bail can be explained and facilitated by the communication system. Real time audio and video feeds of the communication system can be used by the individual to post bail. For example, the individual may enable payment of the entire bail amount to the court, or provide the court a security interest in real property, or contract with a bail bondsman to post the bail. For example, in response to a verbal input from the detainee to the virtual assistant (for example, "contact bond company"), the communication system contacts a bail bond company, the bond company may post the bond and transmit a confirmation of bond payment back to the communication system. The processing and posting of bail may also be performed by the vehicle communication system using a virtual assistant and payment processing device, thereby minimizing delays in court room judicial proceedings. For example, banking information and pin codes may be entered to a payment processing device within the vehicle and/or verbally provided to the virtual assistant. The virtual assistant is used to facilitate the process and is not intended to be a replacement to legal counsel or perform any unauthorized practice of law.

In accordance with the embodiments, the detainee 114 is automatically driven at 140 to an approved location as determined by the mobile proceedings. For example, the detainee 114 may be automatically driven by the self-driving vehicle 122 to an approved location, such as a jail, shelter, or home. Thus, holding facility space need not be taken up.

Figure 2:
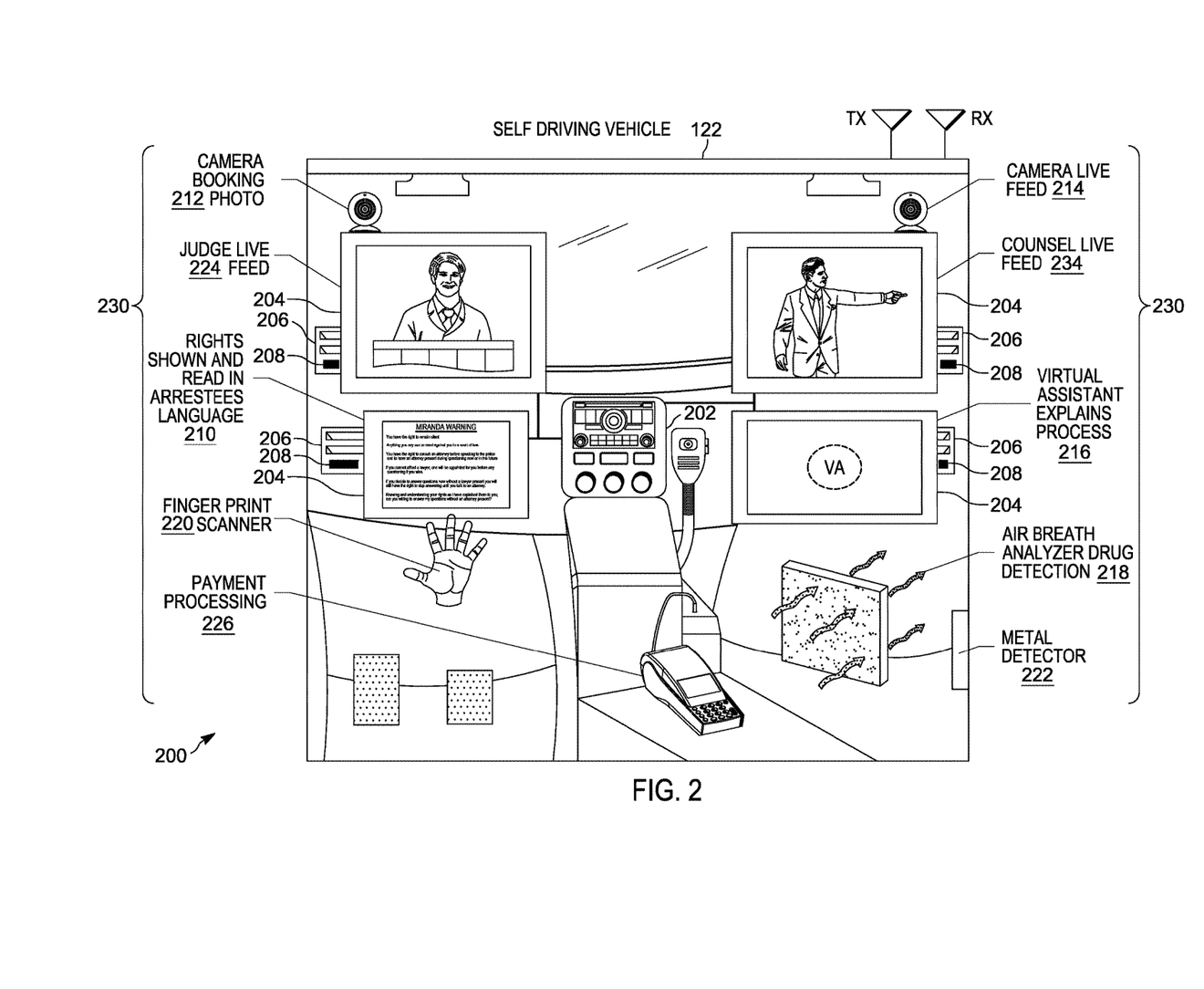
FIG. 2 is a diagram of a mobile law enforcement communication system formed and operating in accordance with various embodiments.

FIG. 2 shows a mobile communication system 200 comprising various components formed and operating in accordance with the various embodiments. A portion of the self-driving vehicle 122 of FIG. 1 is shown in FIG. 2. Mobile communication system 200 comprises the self-driving vehicle 122 of FIG. 1 within which is located a controller device 202 comprising electronic processor, software and data analytics along, which along with transmitters and receivers (shown in FIG. 3) interface with a plurality of interface devices 230 also located within the self-driving vehicle. In accordance with the embodiments, the plurality of interface devices 230 are configured to acquire input pertaining to a detainee within the self-driving vehicle and a law enforcement infraction associated with the detainee. The electronic processor of controller device 202 is programmed to receive the acquired input pertaining to the detainee and the law enforcement infraction. In accordance with the embodiments, the electronic processor enables law enforcement processes and proceedings via the plurality of interface devices located within the self-driving vehicle, including the delivery of the detainee to an approved location determined by the law enforcement processes and proceedings.

The plurality of interface devices 230 comprises one or more displays 204 with corresponding audio interfaces, such as speakers 206 and microphones 208. In accordance with the embodiments, the plurality of interface devices 230 further comprises a camera 212 for taking a photo of the detainee, such as a booking photo, and a video recorder 214 for recording live video and audio feeds where appropriate. In accordance with the embodiments, the plurality of interface devices 230 further comprises a virtual assistant 216 to explain processes and proceedings to the detainee including the reading and visual presentation of legal rights. The virtual assistant 216 can expedite processing of the detainee based on infraction information input by law enforcement upon placement of the individual within the vehicle. For example, a verbal command by the officer to the virtual assistant stating "virtual assistant, process detainee under drunk driving" would initiate a series of testing and inquiries by the communication system 200 upon the detainee. In accordance with the embodiments the plurality of interface devices 230 further comprise air breathalyzers 218 for alcohol and drug detection, a fingerprint scanner 220, a metal detector 222 for detecting weapons. Depending on the type of infraction, the system further provides an automated payment processing feature 226 (which may be a payment processing device or payment processing interface) for posting bonds or paying fines.

Upon entry of the detained individual into the vehicle, the communication system inquires and automatically detects, via virtual assistant 216, the individual's primary language whereupon one or more of the speakers 206 plays out legal rights in that language and one or more of the displays 204 displays legal rights 210. For example, the virtual assistant 216 can detect words spoken by the detainee and utilize language recognition to determine the detainee's primary language. In the United States, the legal rights are referred to as Miranda warnings. The Miranda warnings advise a suspect of his rights, including the right to remain silent, the right to have an attorney present during questioning, and the right to have an attorney provided by the state if unable to afford one. In accordance with the embodiments, the legal rights are provided to the detained individual in his own native language within the vehicle. The legal rights have thus been both read and displayed thereby ensuring that an individual has been given clear warnings. The virtual assistant 216 further explains processes and proceedings taking place within the vehicle, based on the infraction entered by the officer.

In response to invoking a detainee invoking his right to an attorney, the communication system, in conjunction with virtual assistant 216 having artificial intelligence may generate a query to the detainee as to assignment of counsel, via public defender or pre-existing counsel. For example, the communication system may assign a public defender to the detainee, upon the detainee's request of "I want an attorney." Alternatively, the virtual assistant 216 may place a call to the detainee's pre-existing counsel, in response to an input of "contact my attorney" followed by the attorney name. The virtual assistant 216 may answer detainee inquiries pertaining to the mobile adjudication process, such as for example "where am I going?", "I want an attorney", and/or "contact my attorney, John Doe". The virtual assistant can expedite processing of the detainee based on infraction information input by law enforcement but is not intended as a substitute for legal counsel. Legal counsel is provided through a live audio and video feed with a remote attorney 234, shown on one of the displays 204.

In the past, following an arrest, an officer may have searched the detained individual, including reaching into pockets or a bag. However, searching an individual can pose a threat to the officer in cases involving weapons and/or drugs, such as knives or needles. The vehicular communication system of the embodiments facilitates initial detection of alcohol and/or drugs via the air breath analyzer drug detection 218. The vehicular communication system further facilitates initial detection of metal devices, such as weapons or needles, via metal detector 222. The results of these tests may further trigger automated warrant request generation for review and approval by an on-call, remote judge 224 contacted by the communication system within a communications network.

In accordance with some embodiments, the camera 212 and video recorder 214 under electronic processor control of controller 202 can generate an image and/or real time video feed of the detainee which can be used to facilitate booking of a detainee. Depending on the size of data files being captured, the controller 202 may perform analytics and facial recognition on the captured images and video and transmit results from the mobile communication system 200 over a network. In other embodiments, the images and/or video (or portions thereof) may be transmitted from the mobile communication system 200 over a network for facial recognition analysis to take place at a remote base station, server or cloud based network.

Communication system 200 can search and retrieve criminal records and outstanding warrant information pertaining to the detainee based on that facial recognition. The criminal records and warrant information may be stored locally within a memory of the communication system 200 or stored in a cloud based secure vault of a communications network. Behavior, demeanor and body movements or gestures of the detainee can also be recorded and analytics performed to generate behavioral analysis profiles.

For those individuals who are handcuffed, processes and proceedings can take place using voice interaction. Facial analytics can be used to facilitate facial recognition for past records, parole violations, and outstanding warrants. Fingerprint scanning of non-handcuffed individuals can be accomplished via touched data entry or finger taps to any of the displays 204 to further facilitate background verification, parole violations, and/or outstanding warrant checks.

The self-driving vehicle provides for a secured environment where communications may initially take place between the detainee and the virtual assistant. Further communications, may also take place through live video and audio feed communications between the detainee and the detainee's remote counsel 234. Additional communications may take place between the detainee's remote attorney 234, the detainee 114, and the on-call, remote judge 224 over a live video/audio feed. For example arraignment proceedings in which guilty, not guilty or other pleadings may be entered and bond set (or denied).

The communication system 200 further comprises automated payment processing 226 for payment of fines or posting of bail. If the detainee does not have sufficient credit to pay the fine or post bail, the virtual assistant may also utilize artificial intelligence and to analyze an entry (voice), "contact a bond company". The bail bond company can process and post bail (or deny the request) as part of the mobile adjudication process. Upon payment of the fine or bail, the detainee is then driven by the self-driving vehicle 122 to an approved location, such as a home or shelter, as communicated by the on-call, remote judge 224 to the communication system.

In accordance with further embodiments, the self-driving vehicle can pick up the previously detained individual at a later date for a hearing. Hence, in accordance with some embodiments, the self-driving vehicle may drive to a predetermined approved location on a scheduled court date to pick up a formerly detained individual to be driven to a court room hearing.

Figure 3:
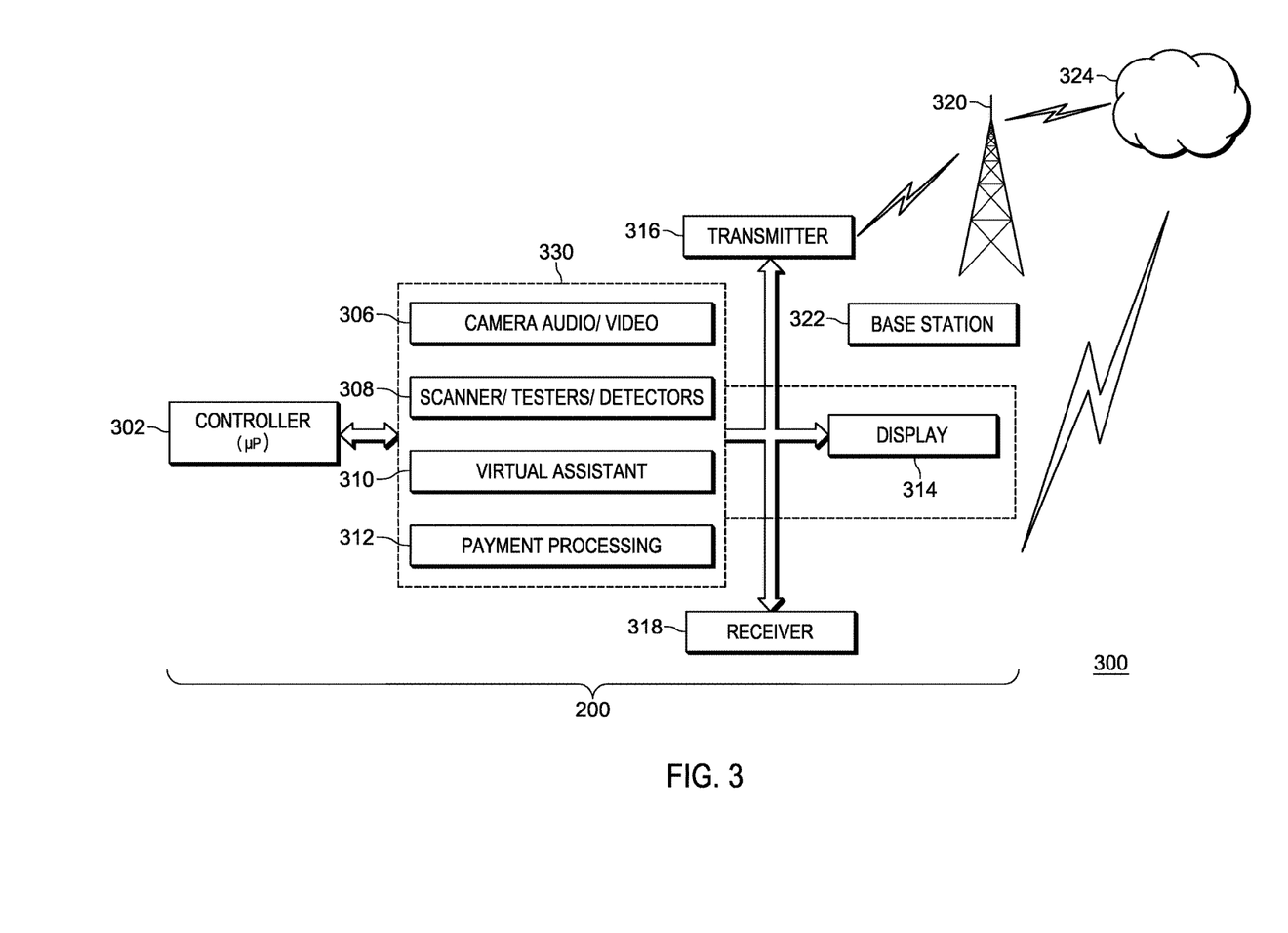
FIG. 3 is a block diagram of the mobile law enforcement communication system operating within one or more communications networks in accordance with various embodiments.

The vehicular communication system 200 is operational within one or more communications networks. FIG. 3 is a block diagram of the vehicular communication system 200 operating within one or more communications networks 300 in accordance with various embodiments. Vehicular communications system 200 comprises one or more controllers 302 providing electronic processors, software, and data analytics for interfacing and controlling a plurality of interface devices 330, such as camera and audio and video components 306, scanners, testers and detectors 308, virtual assistant 310, payment processing 312, and one or more displays 314. In accordance with some embodiments, the controller 302 interoperates with the camera, audio and video components 306 to perform facial recognition and analytics. The scanners, testers and detectors 308 provide fingerprint scanning, alcohol, drug testing, and weapon detection, wherein results are analyzed via the controller 302 in real-time and communicated as appropriate to the one or more communication networks 300. For example, a photo taken of the detainee can be run through a 'most wanted' list within the communications network 300. The one or more controllers 302 may control the virtual assistant 310, with artificial intelligence associated therewith, to provide appropriate responses to inquiries raised by a detainee located within the self-driving vehicle. For example, the virtual assistant 310 can explain and/or answer inquiries pertaining to the mobile law enforcement processes and proceedings taking place within the vehicle. The virtual assistant 310 may further contact court-approved contacts, such as bail bond companies. The one or more controllers 302 may further control payment processing 312, such as posting of bail and/or payment of fines. One or more displays 314 and audio processing interoperate as previously described with the virtual assistant to provide a visual and audible interface presenting legal rights, access to remote counsel, and access to an on-call judge all in the detainee's primary language. The audio translations and text translations made in the individual's preferred language ensure proper delivery of procedures and legal rights to a detainee. Upon conclusion of the proceedings, the virtual assistant 310 receive instructions by the on-call judge for delivery of the individual to an approved court ordered location, via the self-driving vehicle.

The one or more controllers 302 and plurality of interface devices 330 interoperate with one or more transmitters 316 and receivers 318 to allow for the execution of computer programs, and provide, input-output control, file and data management, memory management, communication control and related services for operation within the one or more communications networks 300. For example, the one or more controllers 302 receives instructions, such as from the judge, that enable the self-driving car to drive the individual to a predetermined approved location, such as to a jail, shelter, or home.

The one or more communication networks 300, may comprise for example, communication towers 320, base stations 322, cloud based systems 324 and other infrastructure known or yet to be developed, providing access to other computer law enforcement networks, servers, storage, applications and services. Vehicular communication system 200 operating within the one or more communications networks 300 may operate using one or more suitable communication protocols, techniques, or methodologies, including, without limitation: radio frequency (RF); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; Long Term Evolution (LTE); cellular/wireless/cordless telecommunication protocols (e.g. 3G/4G, etc.); wireless home network communication protocols; satellite data communication protocols; proprietary wireless data communication protocols and any other communication protocols, known or yet to be developed. The memory may include any of volatile memory elements (e.g., random access memory (RAM, such as DRAM, SRAM, SDRAM, etc.)), nonvolatile memory elements (e.g., ROM, hard drive, etc.), and combinations thereof.

Accordingly, there has been provided an improved approach to processing incidents or infractions in an efficient and expedient manner. The access to data and services provided by the mobile vehicular communication system advantageously allows law enforcement officers to remain at a scene, minimizes usage of holding facilities, and reduces court time.

In the foregoing specification, specific embodiments have been described. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises", "comprising", "has", "having", "includes", "including", "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description as part of the original disclosure, and remain so even if cancelled from the claims during prosecution of the application, with each claim standing on its own as a separately claimed subject matter. Furthermore, subject matter not shown should not be assumed to be necessarily present, and that in some instances it may become necessary to define the claims by use of negative limitations, which are supported herein by merely not showing the subject matter disclaimed in such negative limitations.

We claim:

1. A communication system, comprising:
    a self-driving vehicle within which to detain a detainee by a law enforcement officer;
    a plurality of interface devices located within the self-driving vehicle, the plurality of interface devices configured to acquire input pertaining to the detainee within the self-driving vehicle and an infraction associated with the detainee while the law enforcement officer remains in the field; and
    an electronic processor located within the self-driving vehicle, the electronic processor programmed to receive the acquired input pertaining to the detainee and the infraction, and the electronic processor enabling mobile law enforcement processes and proceedings via the plurality of interface devices located within the self-driving vehicle, the mobile law enforcement processes and proceedings providing both a virtual assistant to the detainee along with an interface to an on-call, remote judge and attorney for real-time mobile adjudication of the detainee within the self-driving vehicle and further providing delivery of the detainee to an approved location determined by the mobile law enforcement processes and proceedings.

2. The communication system of claim 1, wherein the plurality of interface devices comprises:
    the virtual assistant coupled to the electronic processor, the virtual assistant automatically transmitting legal rights to the detainee both visually via a display and audibly via a speaker, and wherein the legal rights are provided in a primary language of the detainee as detected by the virtual assistant.

3. The communication system of claim 1, wherein the plurality of interface devices comprises:
    the virtual assistant for describing the mobile law enforcement processes and proceedings to the detainee and answering inquiries from the detainee pertaining to the mobile law enforcement processes and proceedings.

4. The communication system of claim 1, wherein the plurality of interface devices comprises:
    the virtual assistant that receives infraction information input by law enforcement.

5. The communication system of claim 1, wherein the plurality of interface devices further comprises:
    a video recorder taking video recordings of the detainee; and
    the electronic processor performing facial recognition and behavioral analysis of the detainee.

6. The communication system of claim 5, wherein the communication system searches and retrieves criminal records and warrant information pertaining to the detainee based on the facial recognition.

7. The communication system of claim 1, wherein the plurality of interface devices further comprises:
    a breathalyzer located within the self-driving vehicle for automatically measuring an alcohol level of the detainee.

8. The communication system of claim 1, wherein the plurality of interface devices further comprises:
    a finger print scanner located within the self-driving vehicle for scanning fingerprints of the detainee and providing a police background check based on the scanned fingerprints.

9. The communication system of claim 1, wherein the plurality of interface devices further comprises:
    one or more displays located within the self-driving vehicle for presenting legal rights to the detainee; and
    responsive to the detainee invoking a right to an attorney, the virtual the assistant generating a query as to pre-existing counsel, and responsive to identification of pre-existing counsel by the detainee, the virtual assistant contacting the identified pre-existing counsel and setting up a real-time audio and display interface between the detainee and the pre-existing counsel within the self-driving vehicle.

10. The communication system of claim 1, wherein the plurality of interface devices further comprises:
    one or more displays located within the self-driving vehicle for presenting legal rights to the detainee; and
    responsive to the detainee invoking a right to an attorney and not having an attorney, the virtual assistant assigns a public defender and the communication system contacts the public defender.

11. The communication system of claim 10, wherein the communication system automatically transmits pertinent information about the detainee to the public defender.

12. The communication system of claim 11, wherein the plurality of interface devices further comprises:
    one or more displays, wherein at least one of the displays provides a real-time display interface to the public defender.

13. The communication system of claim 1, wherein the plurality of interface devices further comprises:
    an automated payment processing device located within the self-driving vehicle for payment of fines or bail.

14. The communication system of claim 1, wherein the plurality of interface devices further comprises:
    in response to a verbal request from the detainee to the virtual assistant, the communication system automatically contacts a bail bond company.

15. The communication system of claim 14, wherein the bail bond company posts a bond for the detainee in response to the verbal request and confirms bond payment to the communication system.

16. The communication system of claim 1, wherein the approved location for the detainee is transmitted by the remote, on-call judge to the communication system of the self-driving vehicle.

17. The communication system of claim 1, wherein the self-driving vehicle delivers the detainee to the approved location comprising at least one of:
    automatically driving the detainee to a home or shelter;
    automatically driving the detainee to a police station; and
    automatically driving the detainee to jail.

18. The communication system of claim 1, wherein, the mobile proceedings are stored in a memory of the communication system as part of a court proceeding record, and wherein mobile communications take place between only the remote attorney and the detainee within the self-driving vehicle are not stored thereby maintaining attorney client privilege.

19. The communication system of claim 1, wherein the self-driving vehicle drives to a predetermined approved location on a scheduled court date to pick up a formerly detained individual to be driven to a court room hearing.

20. The communication system of claim 1, wherein a warrant request is automatically submitted from the communication system of the self-driving vehicle to the remote on-call judge, in response to the communication system detecting at least one of: weapons, illegal drugs, and exceeded alcohol level thresholds pertaining to the detainee.

21. A method, comprising:
    detaining a detainee within a self-driving vehicle by a law enforcement officer;
    performing mobile law enforcement processes and proceedings of the detainee using a communication system within the self-driving vehicle while the law enforcement officer remains in the field, the mobile law enforcement processes and proceedings providing both a virtual assistant along with an interface to an on-call, remote judge and attorney for real-time mobile adjudication of the detainee; and
    automatically driving, via the self-driving vehicle, the detainee to a location approved by the mobile law enforcement processes and proceedings.

22. The method of claim 21, further comprising: automatically submitting a warrant request from the communication system of the self-driving vehicle to the remote on-call judge, in response to the communication system detecting at least one of: weapons, illegal drugs, and exceeded alcohol level thresholds.

\* \* \* \* \*